US011800966B2

(12) United States Patent
Kihara et al.

(10) Patent No.: US 11,800,966 B2
(45) Date of Patent: Oct. 31, 2023

(54) MEDICAL SYSTEM AND MEDICAL SYSTEM OPERATING METHOD

(71) Applicant: OLYMPUS CORPORATION, Hachioji (JP)

(72) Inventors: Naoya Kihara, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 356 days.

(21) Appl. No.: 16/993,858

(22) Filed: Aug. 14, 2020

(65) Prior Publication Data

US 2020/0367733 A1    Nov. 26, 2020

Related U.S. Application Data

(63) Continuation of application No. PCT/JP2019/006554, filed on Feb. 21, 2019.
(Continued)

(51) Int. Cl.
*A61B 1/00* (2006.01)
*A61B 1/045* (2006.01)
(Continued)

(52) U.S. Cl.
CPC ........ *A61B 1/00006* (2013.01); *A61B 1/0004* (2022.02); *A61B 1/0016* (2013.01);
(Continued)

(58) Field of Classification Search
CPC ......... A61B 34/10; A61B 34/20; A61B 90/37; A61B 1/045; A61B 1/00009;
(Continued)

(56) References Cited

U.S. PATENT DOCUMENTS 5,086,401 A * 2/1992 Glassman ............... A61B 34/30
606/88
6,346,940 B1 * 2/2002 Fukunaga ............... G06T 15/20
382/103
(Continued)

FOREIGN PATENT DOCUMENTS

CN      105769109 A    7/2016
CN      106456267 A    2/2017
(Continued)

OTHER PUBLICATIONS

May 21, 2019 International Search Report issued in International Patent Application No. PCT/JP2019/006601.
(Continued)

*Primary Examiner* — Anh Tuan T Nguyen
*Assistant Examiner* — Shankar Raj Ghimire
(74) *Attorney, Agent, or Firm* — Oliff PLC

(57) ABSTRACT

A medical system and an operating method of a medical system are disclosed. The medical system can operate an endoscope to perform an operation task with respect to a site of interest of an organ of concern in response to input from an operator. The medical system includes a controller that can record a model of the organ of concern generated during preoperative planning, and record the names of a plurality of sites in the organ of concern, and corresponding regions or points in the model with respect to a first coordinate system. The controller receives the name of the site of interest, and the operation task; associates the first coordinate system of the model with a second coordinate system of a display space displayed by a display image; and operates the endoscope with respect to the site of interest on the basis of the operation task.

9 Claims, 7 Drawing Sheets

Related U.S. Application Data

(60) Provisional application No. 62/633,190, filed on Feb. 21, 2018.

(51) Int. Cl.

| | | |
|---|---|---|
| *A61B 1/313* | (2006.01) | |
| *A61B 34/10* | (2016.01) | |
| *A61B 34/20* | (2016.01) | |
| *A61B 34/30* | (2016.01) | |
| *A61B 90/00* | (2016.01) | |

(52) U.S. Cl.
CPC .... *A61B 1/00045* (2013.01); *A61B 1/000094* (2022.02); *A61B 1/045* (2013.01); *A61B 1/3132* (2013.01); *A61B 34/10* (2016.02); *A61B 34/20* (2016.02); *A61B 34/30* (2016.02); *A61B 90/37* (2016.02); *A61B 2034/105* (2016.02); *A61B 2034/107* (2016.02); *A61B 2034/2065* (2016.02); *A61B 2034/301* (2016.02)

(58) Field of Classification Search
CPC . A61B 1/00045; A61B 1/0016; A61B 1/3132; A61B 34/30; A61B 2034/105; A61B 2034/107
See application file for complete search history.

(56) References Cited

U.S. PATENT DOCUMENTS

| | | | | |
|---|---|---|---|---|
| 7,395,249 | B2* | 7/2008 | Wang | A61B 1/0016 |
| | | | | 706/14 |
| 2003/0108853 | A1* | 6/2003 | Chosack | G06T 17/00 |
| | | | | 434/262 |
| 2006/0247520 | A1* | 11/2006 | McGee | A61B 34/20 |
| | | | | 600/434 |
| 2009/0161927 | A1* | 6/2009 | Mori | A61B 6/466 |
| | | | | 382/128 |
| 2009/0227864 | A1 | 9/2009 | Sato et al. | |
| 2010/0312096 | A1* | 12/2010 | Guttman | A61B 34/25 |
| | | | | 600/411 |
| 2011/0054300 | A1 | 3/2011 | Yamamoto et al. | |
| 2012/0081367 | A1* | 4/2012 | Kubota | G06T 7/74 |
| | | | | 345/419 |
| 2014/0051986 | A1* | 2/2014 | Zhao | G06T 7/33 |
| | | | | 600/424 |
| 2014/0092089 | A1* | 4/2014 | Kasuya | G16H 50/50 |
| | | | | 345/420 |
| 2014/0147807 | A1* | 5/2014 | Yau | A61B 34/10 |
| | | | | 433/173 |
| 2014/0153747 | A1 | 6/2014 | Contolini et al. | |
| 2014/0336501 | A1* | 11/2014 | Masumoto | A61B 1/0005 |
| | | | | 600/417 |
| 2015/0073265 | A1* | 3/2015 | Popovic | A61B 34/20 |
| | | | | 600/424 |
| 2015/0305828 | A1* | 10/2015 | Park | G09G 5/377 |
| | | | | 345/629 |
| 2017/0035517 | A1* | 2/2017 | Geri | A61B 34/20 |
| 2017/0172662 | A1* | 6/2017 | Panescu | A61B 34/37 |
| 2017/0181808 | A1* | 6/2017 | Panescu | A61B 1/04 |
| 2017/0273549 | A1* | 9/2017 | Nazareth | A61B 1/06 |
| 2017/0336635 | A1* | 11/2017 | Yoon | H04N 21/2347 |
| 2018/0168755 | A1* | 6/2018 | Cagle | A61B 34/74 |
| 2019/0336222 | A1* | 11/2019 | Schneider | A61B 34/10 |
| 2021/0038340 | A1* | 2/2021 | Itkowitz | A61B 34/25 |
| 2021/0186355 | A1* | 6/2021 | Ben-Yishai | A61B 34/20 |
| 2022/0007919 | A1* | 1/2022 | Prisco | A61B 5/065 |
| 2022/0175537 | A1* | 6/2022 | Fanson | A61B 34/25 |
| 2022/0241013 | A1* | 8/2022 | Panescu | A61B 34/35 |

FOREIGN PATENT DOCUMENTS

| | | |
|---|---|---|
| EP | 2904958 A1 | 8/2015 |
| EP | 3040015 A1 | 7/2016 |
| EP | 3245932 A1 | 11/2017 |
| JP | 2009-213613 A | 9/2009 |
| JP | 2010-274044 A | 12/2010 |
| JP | 2015-047309 A | 3/2015 |
| JP | 2015-093147 A | 5/2015 |
| JP | 2015-514492 A | 5/2015 |
| JP | 2015-514494 A | 5/2015 |
| JP | 2015-530903 A | 10/2015 |
| JP | 2017-508499 A | 3/2017 |
| JP | 2017-511187 A | 4/2017 |
| WO | 2007/091464 A1 | 8/2007 |
| WO | 2007/129493 A1 | 11/2007 |
| WO | 2013/156893 A1 | 10/2013 |
| WO | 2013/157006 A1 | 10/2013 |
| WO | 2014/028394 A1 | 2/2014 |
| WO | 2014/141968 A1 | 9/2014 |
| WO | 2015/029970 A1 | 3/2015 |
| WO | 2015/110934 A1 | 7/2015 |
| WO | 2015/153174 A1 | 10/2015 |
| WO | 2017/006708 A1 | 1/2017 |

OTHER PUBLICATIONS

Apr. 9, 2019 International Search Report issued in International Patent Application No. PCT/JP2019/006554.

Jan. 3, 2023 Office Action issued in Chinese Patent Application No. 201980013735.9.

Jun. 30, 2023 Office Action issued in Chinese Patent Application No. 201980013735.9.

* cited by examiner

MEDICAL SYSTEM AND MEDICAL SYSTEM OPERATING METHOD

CROSS REFERENCE TO RELATED APPLICATIONS

This application is a continuation application based on PCT Patent Application No. PCT/JP2019/006554, filed on Feb. 21, 2019, priority of which is claimed on U.S. Provisional Patent Application No. 62/633,190, filed Feb. 21, 2018. The contents of both the PCT Patent Application and the United States Patent Application are incorporated herein by reference.

BACKGROUND

Technical Field

The present disclosure relates to a medical system for performing a treatment through a hole formed in an abdominal wall or the like and a method for operating the medical system.

Background Art

Conventionally, in laparoscopic surgery, a method of performing a treatment by inserting a treatment tool, an endoscope, or the like through separate holes (openings) formed in an abdominal wall has been used. A scopist operating an endoscope needs to promptly provide an operator with a field of view of the endoscope optimal for treatment, for example, a field of view including a region of interest such as an organ of concern.

SUMMARY

The present disclosure provides a medical system and a method of operating a medical system that support specific operation of a visual field of an endoscope with respect to an organ of concern.

According to an aspect of the present disclosure, a medical system includes: an endoscope that includes an imaging section and can be operated by being electrically driven; a controller that can operate the endoscope and generate a display image from an image captured by the imaging section; a display that can display the display image; and an input device that can receive an instruction for the controller. The controller can record a model of an organ of concern that has been generated during preoperative planning, and can record names of a plurality of sites in the organ of concern, and corresponding regions or points in the model with respect to a first coordinate system. The controller receives from the input device a name of a site of interest among the plurality of sites in the organ of concern, and an operation task to be performed with respect to the site of interest, associates the first coordinate system of the model with a second coordinate system of a display space displayed by the display image, calculates, from a position of the site of interest in the first coordinate system, a position of the site of interest in the second coordinate system, and operates the endoscope with respect to the site of interest based on the operation task.

Another aspect of the present an operating method of a medical system. The method comprises: recording a model of an organ of concern that has been generated during preoperative planning, names of a plurality of sites in the organ of concern, and corresponding regions or points in the model with respect to three-dimensional coordinates of a first coordinate system in association with one another; inputting, via the input device, a name of a site of interest among the plurality of sites in the organ of concern, and an operation task to be performed with respect to the site of interest; associating the first coordinate system of the model with a second coordinate system of a display space displayed by the display image; calculating, from a position of the site of interest in the first coordinate system, a position of the site of interest in the second coordinate system; and operating the endoscope with respect to the site of interest based on the operation task.

According to the medical system and the medical system operating method disclosed herein, specific operation of the visual field of an endoscope with respect to an organ of concern can be supported.

DETAILED DESCRIPTION OF THE PREFERRED EMBODIMENTS

An embodiment of the present disclosure will be described with reference to FIGS. 1 to 9. Dimensions and the like of each component are appropriately adjusted to make the drawings easy to see.

Figure 1:
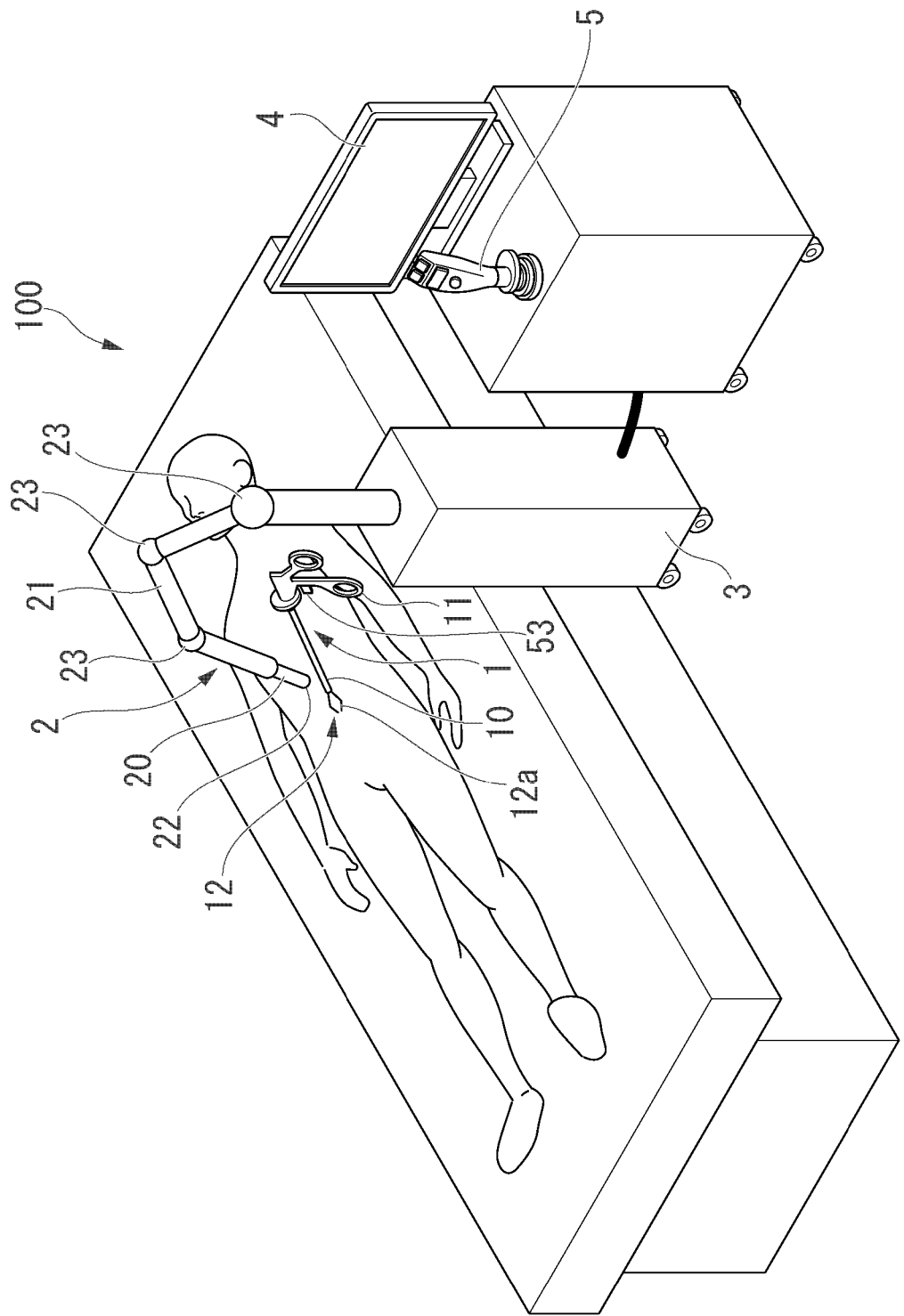
FIG. 1 is a diagram showing an overall configuration of a medical system according to an exemplary embodiment.

FIG. 1 is a diagram showing an overall configuration of a medical system 100 according to the present embodiment.

As shown in FIG. 1, the medical system 100 includes a treatment tool 1, an endoscope 2, a control device 3, a display device 4, and an input device 5. The medical system 100 is a system that supports a treatment performed by inserting the treatment tool 1 and the endoscope 2 through separate holes (openings) formed in the abdominal wall in laparoscopic surgery.

As shown in FIG. 1, the treatment tool 1 has a long insertion portion 10 that can be inserted into a patient's abdominal cavity, and an operation portion 11 provided at a proximal end of the insertion portion 10. The operator passes the insertion portion 10 through a trocar punctured in the abdomen of the patient, and introduces the insertion portion 10 into the abdominal cavity. Depending on the type of treatment and the condition of the affected part, the operator may introduce a plurality of treatment tools 1 into the abdominal cavity.

As shown in FIG. 1, the insertion portion 10 has a treatment portion 12 at the distal end that treats an affected part of a patient. In the present embodiment, the treatment portion 12 is a gripping mechanism including a pair of gripping members 12a.

The operation portion 11 is a member that operates the pair of gripping members 12a. The operation portion 11 has a handle. The pair of gripping members 12a of the treatment portion 12 are opened and closed by moving the handle relatively to the other parts of the operation portion 11. The operator can operate the treatment portion 12 while holding the operation portion 11 with one hand.

Figure 2:
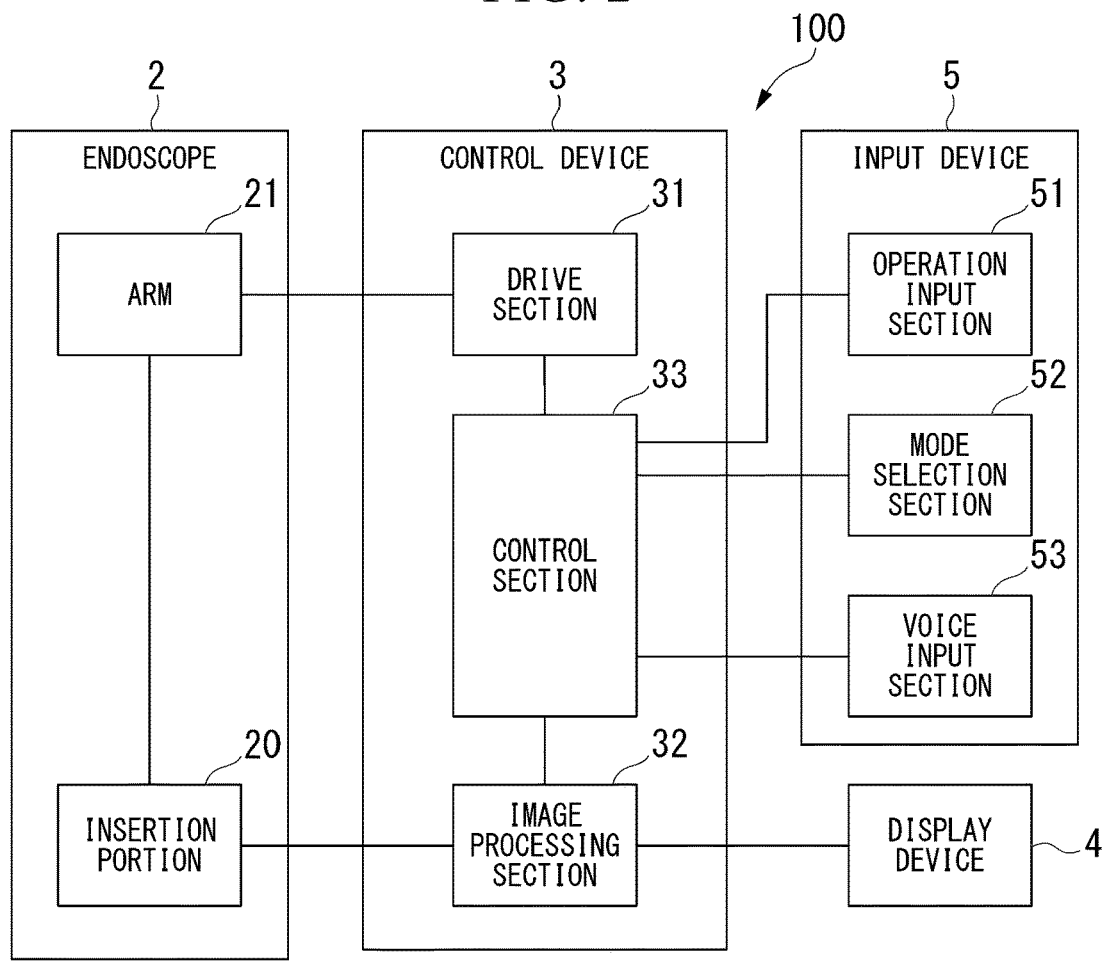
FIG. 2 is a diagram showing a hardware configuration of the medical system.

FIG. 2 is a diagram showing a hardware configuration of the medical system 100 excluding the treatment tool 1.

As shown in FIGS. 1 and 2, the endoscope 2 has a long insertion portion 20 that can be inserted into a patient's abdominal cavity, and an arm 21. The operator passes the insertion portion 20 through a trocar punctured in the abdomen of the patient, and introduces the insertion portion 20 into the abdominal cavity.

The insertion portion 20 is provided at the distal end thereof with an imaging section 22 having a lens and an imaging element for photographing the inside of the patient's abdomen. The insertion portion 20 introduced into the abdominal cavity is arranged at a position where the imaging section 22 can photograph the affected part of the abdomen to be treated. The imaging section 22 may have a function of an optical zoom or an electronic zoom.

The insertion portion 20 may further have an active bending portion which bends actively. By bending the active bending portion provided in a part of the insertion portion 20, the direction of the lens and the imaging element of the imaging section 22 can be changed.

The arm 21 is an electrically driven robot arm having at least one or more joints 23 as shown in FIG. 1. The distal end of the arm 21 is connected to the proximal end of the insertion portion 20 of the endoscope, and the arm 21 can move the insertion portion 20.

The joint 23 is a part that bends around the rotation axis, and may be one that actively bends by a motor or the like, or one that passively bends by advancing or retreating a connected wire or the like. Inside the arm 21, a control signal line, a wire, and the like for controlling the bending operation of the joint 23 are wired. Also, inside the arm 21, a control signal line that controls the imaging section 22 and a transmission signal that transfers a captured image captured by the imaging section 22 are wired.

The control device 3 has a drive section 31, an image processing section 32, and a control section 33, as shown in FIG. 2. The control device 3 controls the arm 21 and the like based on an input from the input device 5. The control device 3 generates a display image from the captured image captured by the imaging section 22 of the endoscope 2 and transfers the display image to the display device 4.

The drive section 31 drives the joint 23 of the arm 21 and the insertion portion 20. In a case where the joint 23 actively bends, the control section 33 generates a control signal to the drive section 31 to operate the joint 23. As a result, the joint 23 can be bent by the drive section 31. As another aspect, in a case where the insertion portion 20 has an active bending portion, the control section 33 generates a control signal for controlling the active bending portion. The drive section 31 generates power for operating the active bending portion according to the generated control signal. As a result, the active bending portion can be bent by the power transmitted through the arm 21.

That is, the drive section 31 can change the field of view of the endoscope 2 by driving at least one of the arm 21 and the insertion portion 20.

The image processing section 32 is connected to a transmission signal of a captured image captured by the imaging section 22, and acquires the captured image via the transmission signal. Further, the image processing section 32 generates a display image for display from the captured image. The image processing section 32 may perform image processing such as image format conversion and contrast adjustment on the captured image as needed. The generated display image is transferred to the display device 4 at a predetermined transfer timing.

The image processing section 32 can generate a display image by replacing an image such as a figure or character generated by the control section 33 with a captured image or by superimposing the image on the captured image. For example, the image processing section 32 can generate a display image by superimposing a character image related to a warning to the operator or operation support on the captured image. The image such as the graphic or the character may be generated not by the control section 33 but by the image processing section 32 based on an instruction from the control section 33.

The control section 33 receives an operation of the input device 5 and an image acquired by the image processing section 32 as inputs, and controls the drive section 31 and the image processing section 32 based on the inputs.

In the present embodiment, the control section 33 has two types of operation modes, a manual mode and an automatic mode. The control section 33 controls the drive section 31 and the image processing section 32 based on one operation mode selected from the two operation modes.

The manual mode is an operation mode in which the scopist operates the input device 5 to directly operate the joint 23 of the arm 21 of the endoscope 2 and the like.

The automatic mode is an operation mode in which the joints 23 and the like of the arm 21 of the endoscope 2 are automatically operated by the control section 33 based on the image acquired by the image processing section 32, and the visual field of the endoscope 2 is automatically adjusted.

Figure 3:
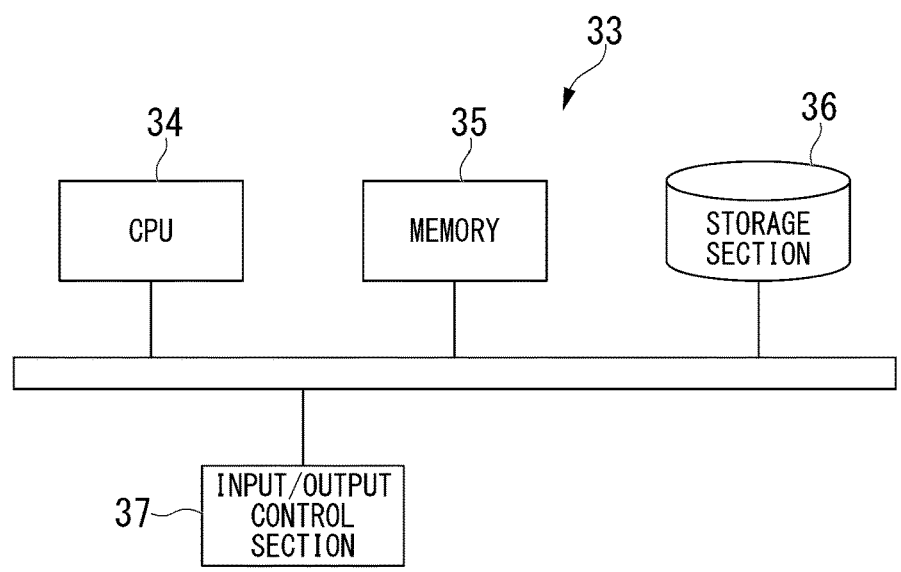
FIG. 3 is a diagram showing an example of the overall configuration of a control section of the medical system.
Figure 4:
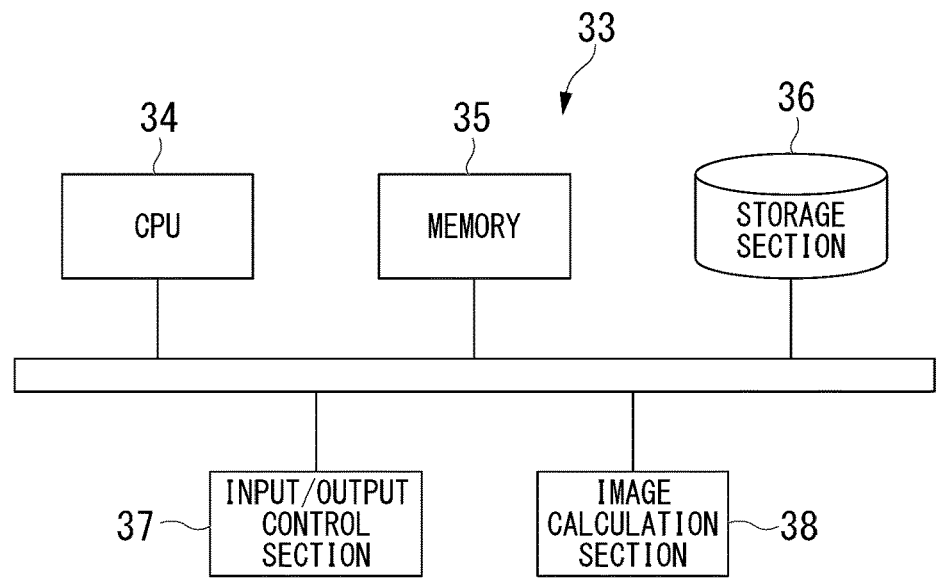
FIG. 4 is a diagram showing an example of the overall configuration of a control section of the medical system.

FIGS. 3 and 4 are diagrams showing an example of the overall configuration of the control section 33.

As shown in FIG. 3, the control section 33 is a program executable device (computer) including a CPU (Central Processing Unit) 34, a memory 35 capable of reading a program, a storage section 36, and an input/output control section 37.

The function of the control section 33 is realized by the CPU 34 executing a program provided to the control section 33. At least a part of the function of the control section 33 may be configured by a dedicated logic circuit or the like.

The storage section 36 is a non-volatile recording medium that stores the above-described programs and necessary data. The storage section 36 includes, for example, a ROM, a hard disk, and the like. The program recorded in the storage section 36 is read into the memory 35 and executed by the CPU 34.

The input/output control section 37 receives input data from the input device 5 and the image processing section 32, and transfers the data to the CPU 34 and the like. In addition, when the CPU 34 controls the drive section 31 and the image processing section 32, the input/output control section 37 generates a control signal and the like for the drive section 31 and the image processing section 32 based on an instruction from the CPU 34.

Here, the control section 33 is not limited to a device provided in one piece of hardware. For example, the control section 33 may be configured by separating the CPU 34, the memory 35, the storage section 36, and the input/output control section 37 as separate hardware, and connecting the hardware via a communication line. Alternatively, the control section 33 may be realized as a cloud system by separating the storage section 36 and connecting the storage section 36 via a communication line.

Here, when the image processing section 32 performs the processing of the captured image, the memory 35 of the control section 33 may be used to store temporary data being processed. Further, a part or all of the processing of the captured image performed by the image processing section 32 may be performed by the CPU 34 of the control section 33 by executing a program.

The control section 33 may further include components necessary for the operation of the control device 3, other than the CPU 34, the memory 35, the storage section 36, and the input/output control section 37 shown in FIG. 3. For example, as shown in FIG. 4, the control section 33 may further include an image calculation section 38 that performs a part or all of the specific image processing and the image recognition processing. By further including the image calculation section 38, the control section 33 can execute specific image processing and image recognition processing at high speed.

The display device 4 is a device that displays a display image generated by the image processing section 32. As the display device 4, a known display device such as an LCD display can be used. The display device 4 may be a head-mounted display or a projector.

The input device 5 includes an operation input section 51, a mode selection section 52, and a voice input section 53, as shown in FIG. 2. The input device 5 is a device for inputting information necessary for the operation of the medical system 100.

The operation input section 51 is a device for inputting an operation of the joint 23 of the arm 21 of the endoscope 2. When the imaging section 22 has a zoom function, the operation input section 51 can also operate the zoom function. Also, the scopist can operate the operation input section 51 to operate the joint 23 of the arm 21 and the like.

The operation input section 51 may be configured by a joystick or may be configured by a touch panel, as shown in FIG. 1. It may be an operation input device having an arm shape similar to the arm 21. The display device 4 of the LCD display and the operation input section 51 of the touch panel may be integrally configured.

By operating the operation input section 51, the contents of the operation are transferred to the control section 33. The control section 33 calculates an operation amount of the arm joint 23 corresponding to the operation content. The control section 33 controls the drive section 31 so that the joint 23 operates with the calculated amount of operation.

When the operation mode of the control section 33 is the manual mode, the joint 23 and the like of the arm 21 of the endoscope 2 are directly operated by the operation of the operation input section 51.

On the other hand, when the operation mode of the control section 33 is the automatic mode, the operation of the operation input section 51 is invalidated by the control section 33, and the joint 23 and the like of the arm 21 of the endoscope 2 cannot be operated. The joint 23 and the like of the arm 21 of the endoscope 2 are operated by the control section 33.

The mode selection section 52 is a device that selects which of the two operation modes of the control section 33 the control section 33 operates in. The mode selection section 52 may be configured by a switch or may be configured by a touch panel. Further, the mode selection section 52 may be configured integrally with the operation input section 51. The operation mode selection of the control section 33 by the mode selection section 52 can be performed at any time.

The audio input section 53 includes a component such as a microphone that converts the input audio into a signal, and transfers the signalized audio signal to the control section 33.

(Operation of Medical System 100)

The operation and the operating method of the medical system 100 will be described with reference to FIGS. 5 to 9 by taking laparoscopic surgery as an example. In the present embodiment, the organ of concern is the liver L.

Prior to laparoscopic surgery, the operator or the like performs a preoperative plan for generating a model (shape data or image) of the organ of concern using a known method. The operator or the like generates three-dimensional shape data of the organ of concern from a plurality of CT images, for example. The three-dimensional coordinate system of the three-dimensional shape data generated in the preoperative plan is referred to as "model coordinate system (first coordinate system) C1".

Figure 5:
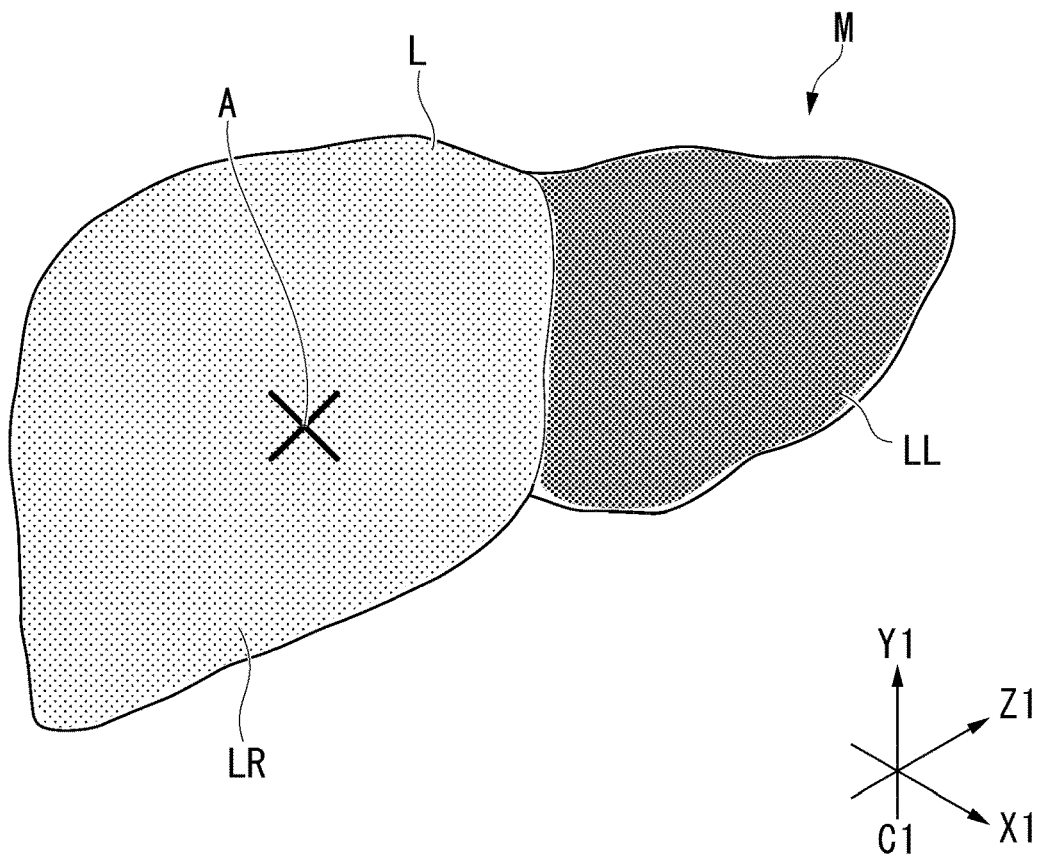
FIG. 5 shows a model of an organ of concern generated in a preoperative plan.

FIG. 5 shows a model M of the organ of concern (liver L) generated in the preoperative plan. The model M is associated with three-dimensional coordinates (X1, Y1, and Z1 coordinates) in the model coordinate system C1, and the position of each part of the model M can be specified by the three-dimensional coordinates in the model coordinate system C1. As shown in FIG. 5, the model M is configured so that the right lobe LR and the left lobe LL are distinguished.

In the preoperative plan, the operator or the like generates a "site database D1" in which (1) the name of the site in the model M and (2) the region of the site in the model coordinate system C1 are registered.

Table 1 is an example of the site database D1.

The name of the site in the site database D1 may be an anatomical name or an abbreviated name. A region in the model coordinate system C1 of the site database D1 is specified by three-dimensional coordinates (X1, Y1, and Z1 coordinates) in the model coordinate system C1. The region in the model coordinate system C1 may specify a voxel region in detail using a plurality of three-dimensional coordinates, may specify a rough region using three-dimensional coordinates of two points, or may specify only the point of interest only by using the three-dimensional coordinates of one point.

TABLE 1

| name of site | region in model coordinate system C1 |
| --- | --- |
| right lobe | (X1, Y1, Z1)~(X2, Y2, Z2) |
| left lobe | (X3, Y3, Z3)~(X4, Y4, Z4) |
| tumor A | (X5, Y5, Z5) |

The operator or the like may set a specific region to be treated or observed in laparoscopic surgery as a "region of interest" in the model M in the preoperative plan. In the present embodiment, as shown in FIG. 5, the region of interest is a tumor A in the right lobe LR of the organ of concern (liver L). When the region of interest is set, as shown in Table 1, the operator or the like adds the tumor A, which is the region of interest, to the site database D1.

Table 2 is an example of the operation task database D2.

The operator or the like generates the "operation task database D2" in the preoperative plan. The operation task database D2 is a database in which the operation tasks of the endoscope 2 such as "enlarged display" and "entire display" and the operation contents of the endoscope 2 corresponding to the operation task are registered. In the operation task database D2, for example, the operation content of the endoscope 2 such as "the imaging section 22 of the endoscope 2 is brought closer to the site of interest" is registered corresponding to the operation task of "entire display".

TABLE 2

| operation task | operation contents of endoscope |
|---|---|
| enlarged display | ... |
| entire display | ... |
| ... | ... |

The model M of the organ of concern generated in the preoperative plan is recorded in the storage section 36 of the control section 33 of the control device 3, in association with the names of a plurality of sites in the organ of concern and the region of the model M in the model coordinate system C1, that is, together with the site database D1 (model recording step). The operation task database D2 is also recorded in the storage section 36 of the control section 33 of the control device 3.

Next, the control device 3 extracts and stores a plurality of feature points F in the model M (a feature point extraction step). The plurality of feature points F are extracted using a known feature point extraction method. The plurality of feature points F are identified and stored in the storage section 36 together with the feature amount calculated according to a predetermined standard suitable for representing the feature, together with the three-dimensional coordinates in the model coordinate system C1. The extraction and storing of the plurality of feature points F may be performed before surgery or may be performed during surgery.

The operation of the medical system 100 during laparoscopic surgery will be described. The operator provides a plurality of holes (openings) for placing a trocar on the abdomen of the patient, and punctures the trocar into the holes. Next, the operator passes the insertion portion 10 of the treatment tool 1 through a trocar punctured in the abdomen of the patient, and introduces the insertion portion 10 into the abdominal cavity.

Next, the scopist operates the mode selection section 52 to set the operation mode of the control section 33 to the manual mode. By operating the operation input section 51 and operating the endoscope 2, the scopist passes the insertion portion 20 of the endoscope 2 through a trocar punctured in the abdomen of the patient, and introduces the insertion portion 20 into the abdominal cavity.

Figure 6:
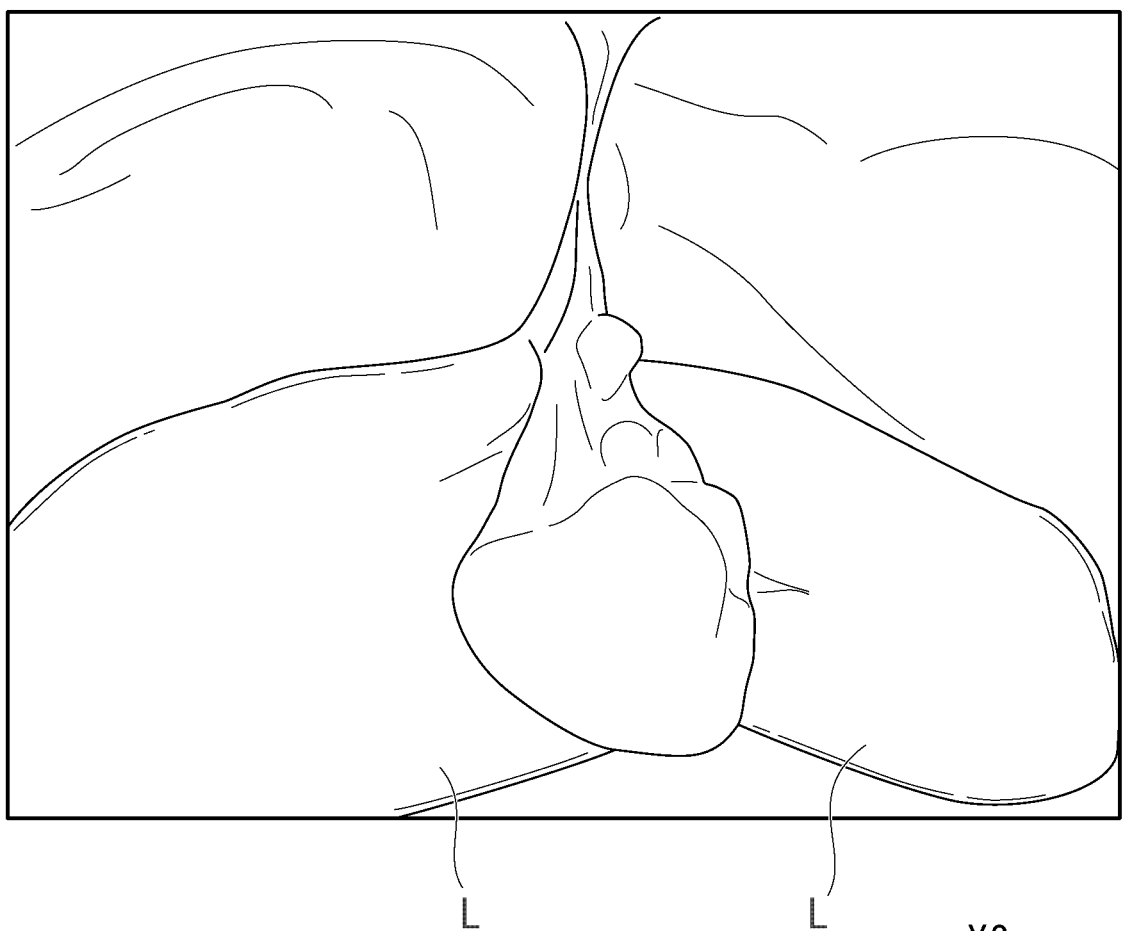
FIG. 6 is a display image generated by the control device from a captured image captured by the endoscope.

FIG. 6 is a display image generated by the control device 3 from a captured image captured by the imaging section 22 of the endoscope 2 inserted into the abdominal cavity. The liver L is displayed on the display image shown in FIG. 6. The three-dimensional coordinate system of the display space displayed by the display image is referred to as "display coordinate system (second coordinate system) C2".

The operator wants to operate the endoscope 2 so that "tumor A", which is the region of interest, is displayed in an enlarged state on the display screen. Therefore, the operator or the scopist operates the mode selection section 52 to change the operation mode of the control section 33 to the automatic mode. The operation of the operation input section 51 is invalidated by the control section 33, and a scopist or the like cannot operate the joint 23 or the like of the arm 21 of the endoscope 2. Hereinafter, description will be given along a control flowchart in the automatic mode shown in FIG. 7.

Figure 7:
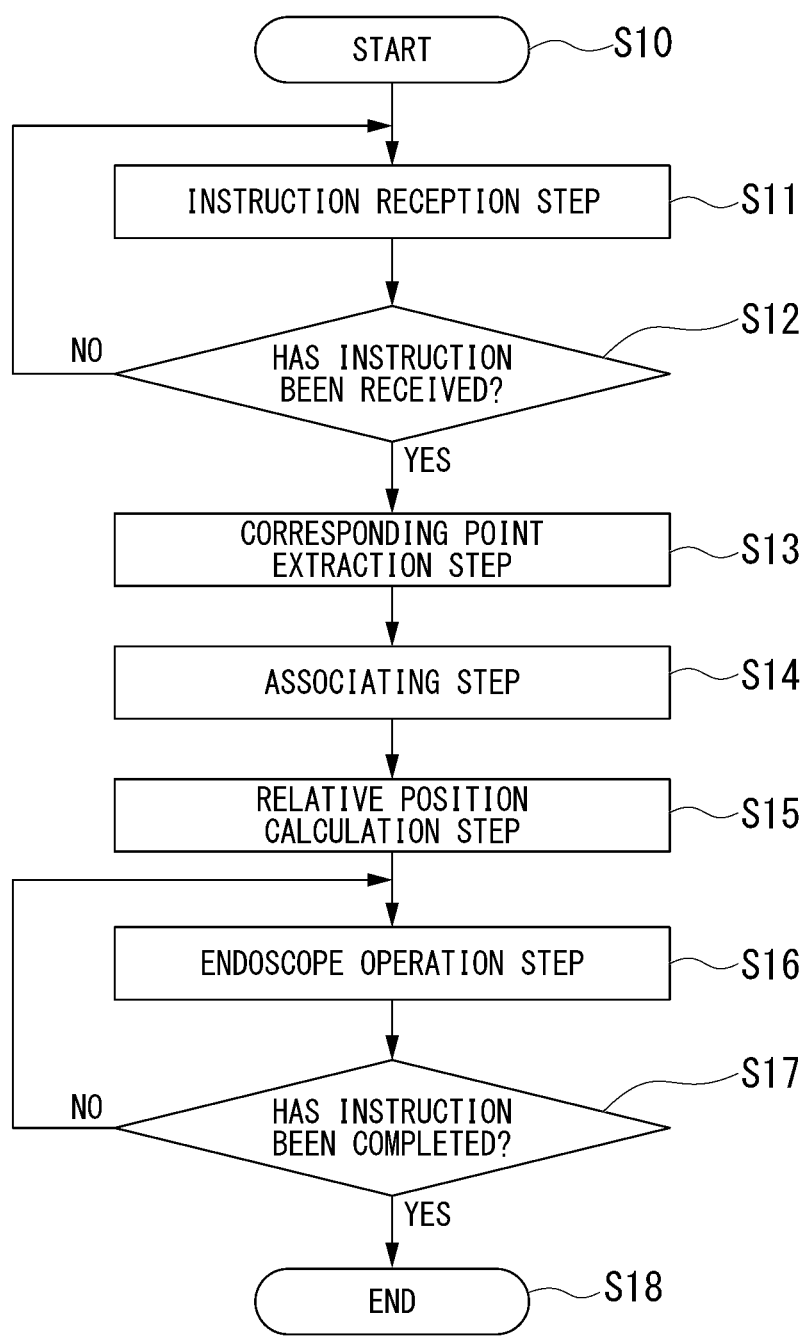
FIG. 7 is a flowchart of a control in an automatic mode of the control section.

As shown in FIG. 7, when the operation mode of the control section 33 is set to the automatic mode, the control section 33 starts control in the automatic mode (step S10). Next, the control section 33 executes step S11.

In step S11, the control section 33 receives, from the voice input section 53, the name of a site of interest among a plurality of sites in the organ of concern and an operation task for the site of interest (instruction reception step). The control section 33 operates the voice input section 53 and receives an instruction by voice input from an operator or the like. The control section 33 performs voice recognition of the voice signal transferred from the voice input section 53 by a known voice recognition method. Next, after a lapse of a predetermined time, the control section 33 executes step S12.

In step S12, the control section 33 determines whether or not the content of the voice recognition includes the "name of site" registered in the site database D1 and the "operation task" registered in the operation task database D2.

When it is determined that it is not included, the control section 33 executes step S11 again.

When it is determined that it is included, the control section 33 next executes step S13.

The "name of site" included in the content of the voice recognition is a part of interest that the operator or the like pays attention to among the sites registered in the site database D1. The "operation task" included in the content of the voice recognition is an operation task for the site of interest. In the present embodiment, it is assumed that "tumor A" has been instructed as the site of interest, and "enlarged display" has been instructed as the operation task for the site of interest.

In step S13, the control section 33 extracts a plurality of corresponding points A corresponding to a plurality of feature points F in the display image (corresponding point extraction step). The control section 33 extracts a plurality of corresponding points A in the display image based on the feature amounts of the plurality of feature points F stored in the storage section 36 in advance. For the extraction processing, a technique appropriately selected from known template matching techniques and the like is used. When the control section 33 includes the image calculation section 38 that performs part or all of the image matching processing at high speed, the above-described matching processing can be executed at high speed. Next, the control section 33 executes step S14.

In step S14, the control section 33 associates the model coordinate system C1 of the model M with the display coordinate system C2 of the display space where the display image is displayed, based on the plurality of feature points F and the plurality of corresponding points A (associating step). In the associating process, a method appropriately selected from known coordinate conversion methods and the like is used. When the associating step is completed, the coordinate position of the model M that can be reached in the first coordinate system C1 can be converted to the display coordinate system C2 in the display space.

Figure 8:
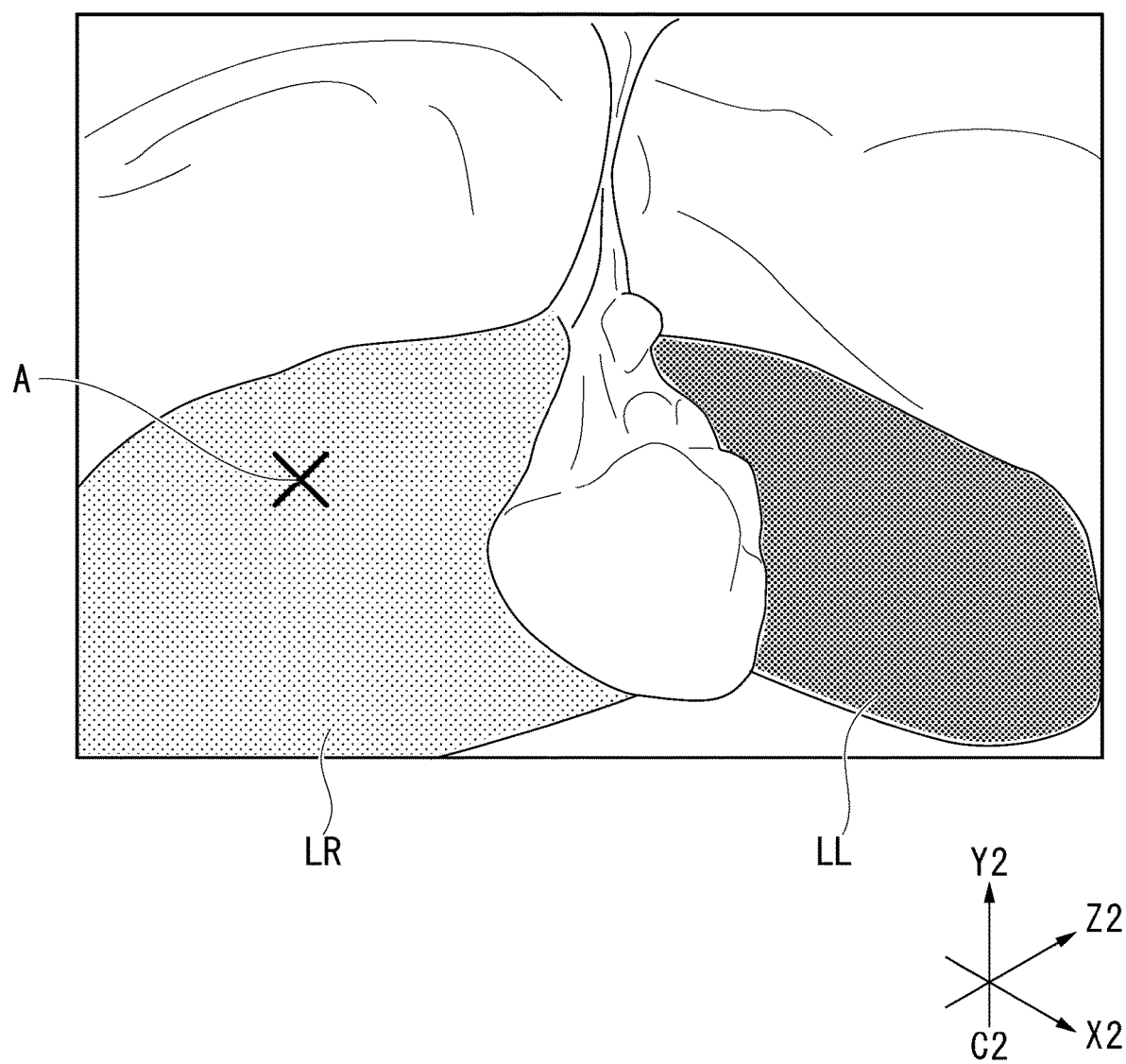
FIG. 8 is a display image after the associating step is completed.

FIG. 8 is a display image after the associating process is completed.

After the completion of the associating step, the coordinate positions of the model M that can be moved to the first coordinate system C1 can be converted to the display coordinate system C2 of the display space. Therefore, the sites (the right lobe LR, the left lobe LL, and the tumor A) registered in the site database D1 shown in Table 1 can specify the region in the display coordinate system C2 of the display space. In the display image shown in FIG. 8, an identification display image (hatched image) in which the positions of the right lobe LR, the left lobe LL, and the tumor A are known is superimposed. Next, the control section 33 executes step S15.

In step S15, the control section 33 calculates the position of the site of interest (tumor A) in the display coordinate system C2, from the position of the site of interest (tumor A) set in the model M in the model coordinate system C1 (relative position calculation step). Next, the control section 33 executes step S16.

In step S16, the control section 33 operates the endoscope 2 on the site of interest (tumor A) based on the instructed operation task (endoscope operation step). Since the instructed operation task is "enlarged display", the control section 33 uses the position of the site of interest in the display coordinate system C2 obtained in step S15, to operate the arm 21 of the endoscope 2 so that the imaging section 22 approaches the position of the site of interest, based on the corresponding "operation contents of the endoscope" registered in the "operation task database D2". Next, the controller 33 executes step S17.

In step S17, the control section 33 determines whether the operation task instructed for the site of interest is completed.

When it is determined that the process has not been completed, the control section 33 executes step S16 again.

When it is determined that the process has been completed, the control section 33 next executes step S18 and ends the automatic mode.

Figure 9:
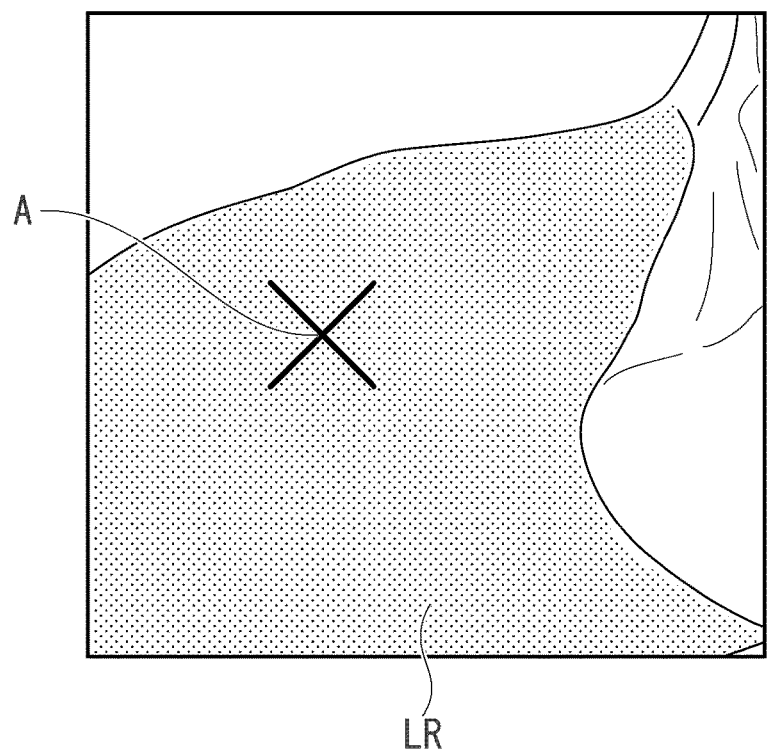
FIG. 9 is a display image after the automatic mode is completed.

FIG. 9 is a display image after the automatic mode is completed.

After the control in the automatic mode is completed, the operation task (enlarged display) instructed for the site of interest (tumor A) specified in the model M generated by the preoperative plan is performed.

According to the medical system 100 of the present embodiment, a specific operation of the visual field of the endoscope 2 with respect to the organ of concern can be supported using the model M generated by the preoperative plan. It is possible to specify a site of interest out of the plurality of sites registered in the site database D1 before the operation, and to specify a specific operation task for the site of interest from the operation task registered in the operation task database D2 before the operation.

Conventionally, the operator has instructed the scopist to change the field of view of the endoscope 2 based on the display image (for example, an instruction to "move the field of view to the right").

On the other hand, the medical system 100 can instruct to change the visual field of the endoscope 2 using the name of the site. Further, the site used for the instruction need not be displayed on the display screen when the instruction is performed. Therefore, the medical system 100 can quickly provide a visual field that meets the operator's desire.

The medical system 100 allows the operator to set information (name, region) on the site of interest in the model M before the surgery, so that the visual field can be quickly secured during the surgery, and the burden on the surgeon and scopist can be reduced.

As described above, an embodiment of the present disclosure has been described in detail with reference to the drawings. However, the specific configuration is not limited to this embodiment, and may include a design change or the like without departing from the gist of the present disclosure. The components shown in the above-described embodiment and the modifications described below can be appropriately combined and configured.

In the above embodiment, the instruction is received by voice in the instruction reception step, but the method of receiving the instruction is not limited to this. For example, the medical system may register only one type of each of the "name of site" and the "operation task", and when receiving a start signal from a foot pedal or the like connected to the input device, it may operate assuming that the contents of the registered "name of site" and "operation task" are instructed.

In the above embodiment, the display image is changed by operating the arm 21 of the endoscope 2 to change the imaging position of the endoscope 2, but the method of changing the display image is not limited to this. The image processing section may have a function of generating a display image by cutting out a partial region from the captured image of the endoscope, and may change the display image by changing the position where the image is cut out. Further, the image processing section may change the display image by controlling the zoom function of the imaging section. Even in the case of an endoscope having no arm, the display image can be changed.

Figure 10:
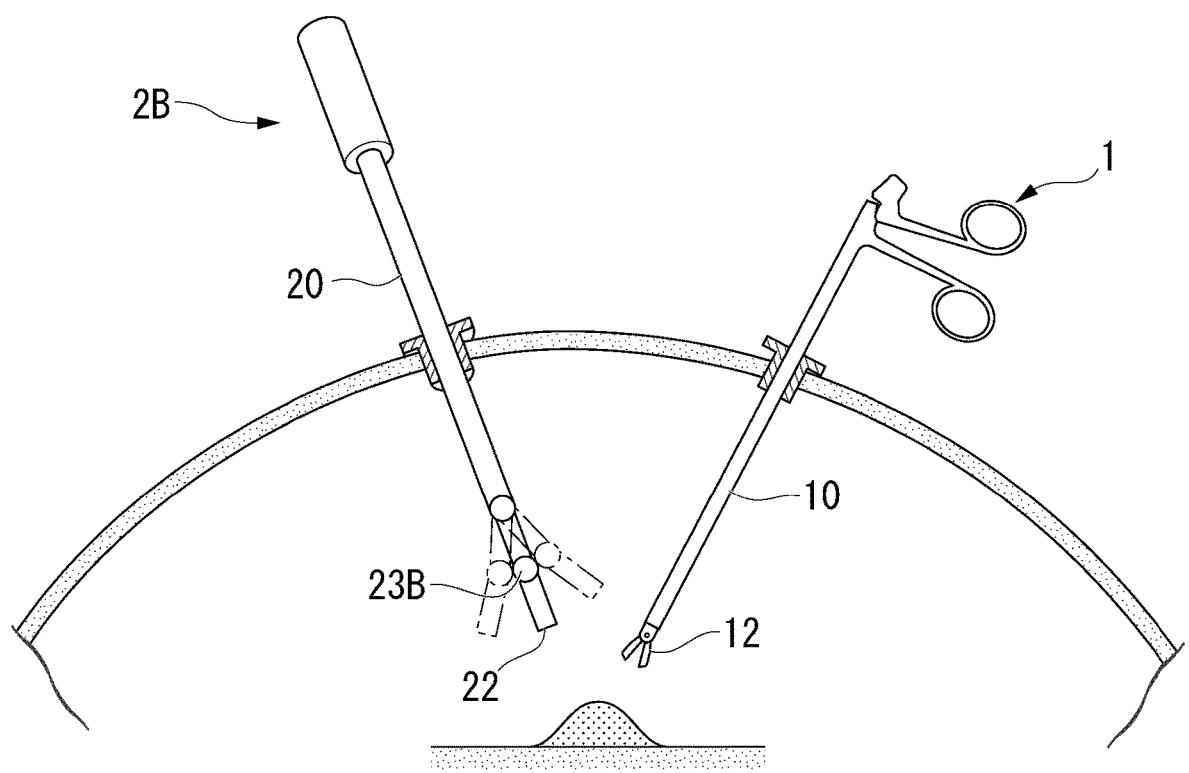
FIG. 10 shows an overall configuration example of a modification of the endoscope.

FIG. 10 is an overall configuration example showing an exemplary endoscope 2B which is a modification of the endoscope 2. The endoscope 2B has an active bending portion 23B at the distal end of the insertion portion 20. The operator can change the position and direction of the imaging section 22 of the endoscope 2 by moving the endoscope 2B while holding the endoscope 2B. In addition, by bending the active bending portion 23B, the position and the direction of the imaging section 22 can be changed. Even when the endoscope 2B is used instead of the endoscope 2, the control section 33 can change the display image by driving the active bending portion 23B.

What is claimed is:

1. A medical system, comprising:
   an endoscope that has an imaging section including a lens and is configured to be operated by being electrically driven;
   a controller configured to operate the endoscope and generate a display image from an image captured by the imaging section;
   a display configured to display the display image; and
   an input device configured to receive an instruction for the controller, the input device including a voice input section that includes a microphone,
   wherein the controller is configured to:
      record a model of an organ of concern generated during preoperative planning, the model being arranged with respect to a first coordinate system,
      record names of a plurality of sites in the organ of concern, and corresponding regions or points in the model that are defined by three-dimensional coordinates of the first coordinate system, the names being recorded in association with the corresponding regions or points, the names including a name of a specific region set by an operator among the names of the plurality of sites in the organ of concern, receive from the input device a name of a site of interest among the plurality of sites in the organ of concern, and an operation task to be performed with respect to the site of interest, the operation task being an operation to change a field of view of the endoscope with respect to the site of interest, associate the first coordinate system of the model with a second coordinate system of a display space displayed by the display image, calculate, from a position of the site of interest in the first coordinate system, a position of the site of interest in the second coordinate system, and operate the endoscope with respect to the site of interest based on the operation task, wherein the voice input section is configured to receive the name of the site of interest and the operation task as a voice input and transfer a corresponding signal to the controller, and wherein, after the name of the site of interest and the operation task are received by the voice input section, the controller is configured to disable an operation of the endoscope different from the operation task of the voice input until the operation task of the voice input is completed.

2. The medical system according to claim 1, wherein the controller is configured to operate the endoscope with respect to the site of interest regardless of whether the site of interest is displayed on the display when the voice input of the name of the site of interest is received by the voice input section.

3. The medical system according to claim 1, wherein the input device further includes a foot pedal and is further configured to receive the name of the site of interest and the operation task input by an operation of the foot pedal.

4. The medical system according to claim 1, wherein the controller is configured to:

record the operation task for the site of interest and a corresponding operation content of the endoscope in association with each other, and operate the endoscope based on the operation content.

5. The medical system according to claim 1, wherein the controller is configured to:

extract, in the display image, a plurality of corresponding feature points corresponding to a plurality of feature points in the model, and associate the first coordinate system of the model with the second coordinate system of the display space displayed by the display image, based on the plurality of feature points and the plurality of corresponding feature points.

6. An operating method of a medical system that includes an endoscope that has an imaging section including a lens and is configured to be driven and operated by electric power, a controller configured to operate the endoscope and generate a display image from an image captured by the imaging section, a display configured to display the display image, and an input device configured to receive an instruction for the controller, the method comprising:

recording a model of an organ of concern generated during preoperative planning, the model being arranged with respect to a first coordinate system, recording names of a plurality of sites in the organ of concern, and corresponding regions or points in the model that are defined by three-dimensional coordinates of the first coordinate system, the names being recorded in association with the corresponding regions or points, the names of the plurality of sites in the organ of concern including a name of a specific region set by an operator;

inputting by a voice input, via the input device, a name of a site of interest among the plurality of sites in the organ of concern, and an operation task to be performed with respect to the site of interest, the operation task being an operation to change a field of view of the endoscope with respect to the site of interest;

after the name of the site of interest and the operation task are input by the voice input, disabling an operation of the endoscope different from the operation task of the voice input until the operation task of the voice input is completed;

associating the first coordinate system of the model with a second coordinate system of a display space displayed by the display image;

calculating, from a position of the site of interest in the first coordinate system, a position of the site of interest in the second coordinate system; and operating the endoscope with respect to the site of interest based on the operation task.

7. The operating method according to claim 6, wherein the name of the site of interest specified by the voice input includes a name of a site that is not displayed on the display.

8. The operating method according to claim 6, further comprising:

recording the operation task for the site of interest and a corresponding operation content of the endoscope in association with each other, and operating the endoscope based on the operation content.

9. The operating method according to claim 6, further comprising:

extracting, in the display image, a plurality of corresponding feature points corresponding to a plurality of feature points in the model, and associating the first coordinate system of the model with the second coordinate system of the display space displayed by the display image, based on the plurality of feature points and the plurality of corresponding feature points.

* * * * *